US006792801B2

(12) United States Patent
Hoggan et al.

(10) Patent No.: US 6,792,801 B2
(45) Date of Patent: Sep. 21, 2004

(54) DEVICE FOR MEASURING FORCE AND ANGLES

(75) Inventors: Lynn D. Hoggan, Sandy, UT (US); John Griffin, Phoenix, AZ (US); Earl Van Wagoner, III, Macon, GA (US); Michael K. Durtschi, Salt Lake County, UT (US)

(73) Assignee: Hoggan Health Industries, Inc., Draper, UT (US)

( * ) Notice: Subject to any disclaimer, the term of this patent is extended or adjusted under 35 U.S.C. 154(b) by 46 days.

(21) Appl. No.: 10/345,738

(22) Filed: Jan. 15, 2003

(65) Prior Publication Data

US 2004/0134274 A1 Jul. 15, 2004

(51) Int. Cl.[7] .................................................. A16B 1/24
(52) U.S. Cl. .................................................. 73/379.02
(58) Field of Search ......................... 73/379.01, 379.02, 73/379.03

(56) References Cited

U.S. PATENT DOCUMENTS

| | | | | |
|---|---|---|---|---|
| 4,037,480 A | * | 7/1977 | Wagner | 73/865.4 |
| 5,038,795 A | * | 8/1991 | Roush et al. | 600/587 |
| 5,090,421 A | | 2/1992 | Wagoner, III | |
| 5,092,584 A | * | 3/1992 | Jones | 482/10 |
| 5,368,546 A | * | 11/1994 | Stark et al. | 601/34 |
| 5,628,722 A | * | 5/1997 | Solomonow et al. | 602/26 |
| 5,697,381 A | * | 12/1997 | Rantala et al. | 600/595 |

* cited by examiner

Primary Examiner—Max Noori
(74) Attorney, Agent, or Firm—Mallinckrodt & Mallinckrodt; Robert R. Mallinckrodt (57) ABSTRACT

Apparatus for selectively testing muscle strength and range of motion of a body part of a patient includes a housing having at least one contact area, and preferably two spaced apart contact areas, for contacting and aligning the apparatus with a body part to be tested for range of motion and an inclinometer to measure the angle of the apparatus and produce an angle signal indicative of the measured angle. The difference between the angle measured at one extreme of movement of the body part and at the other extreme of movement provides a measure of the range of motion. A force applicator coupler couples a force applicator to a force transducer to measure muscle strength. The force transducer produces a force signal indicative of the force applied by the force applicator to the force transducer. Interface circuitry which preferably includes a microprocessor processes the angle signals and the force signals to produce output signals to a display in the apparatus and, if desired, to a computer programmed to receive such signals.

20 Claims, 7 Drawing Sheets

DEVICE FOR MEASURING FORCE AND ANGLES

BACKGROUND OF THE INVENTION

1. Field

The invention is in the field of musculoskeletal testing, particularly the field of muscle strength testing referred to sometimes as Manual Muscle Testing and Computerized Muscle Testing, in range of motion testing, and in tender point evaluation, particularly on human patients.

2. State of the Art

Several instruments are currently available for use by physical therapists, orthopedic surgeons, neurologists, and chiropractors for measuring muscle strength (Manual Muscle Testing or Computerized Muscle Testing) and performing tender point evaluation in human patients. Instruments are also available for measuring range of motion of various body parts in human patients.

Muscle strength testing is used to identify areas of muscular weakness due to injury or disease. The results provide clinicians with valuable information for diagnosis of extent of injury and disability. Range of motion testing provides information as to limitations in movement of body parts such as the back and neck and again provides valuable information for diagnosis of extent of injury and disability. The information may be used to complete and calculate disability ratings and indexes, and compares activities of daily living questionnaires such as the Oswestry Low Back, Neck Pain, Rand 36, and Roland Morris questionnaires. Tender point (algometry) evaluation indicates whether a patient is a candidate for the diagnosis of fibromyalgia pursuant to the American College of Rheumatology standards.

U.S. Pat. No. 5,090,421, issued to one of the inventors hereof and assigned to the assignee of the present invention, describes an apparatus for testing muscle strength which is used extensively for muscle strength testing. It is also used for tender point evaluation. Range of motion testing instruments are also available. There are also several computer programs available for recording the results of such testing and producing reports based on such results. However, separate instruments are used to measure muscle strength and range of motion and where both types of measurements are being taken, as is common in many situations, the person doing the testing must set up the instrument for one type of testing, perform those tests, and then set up the other instrument for and perform the other type of testing. Where the instruments are connected to a computer, one instrument is coupled to the computer and the measurements taken and then the other instrument is coupled to the computer and measurements taken. This extends the time for patient testing, increasing patient discomfort, and increasing the cost both because of the increased time and because of the requirement for two sets of testing equipment.

SUMMARY OF THE INVENTION

According to the invention, the same apparatus is used for both muscle strength testing and range of motion testing. While different sensors are used for each type of measurement in the apparatus, a single microprocessor and the same data transmission circuits are used for determining and reporting the results of such testing.

The apparatus of the invention includes a housing, preferably an ergonomically designed housing sized and configured to easily fit into and be held by a user's hand and having an indentation aligned with the user's thumb when the housing is properly held by a user for range of motion testing. A push button switch is located in the indentation to be thumb operated by the user when a range of motion measurement is desired to be made. While a particular configuration of apparatus is shown in the drawings with a particular configuration of thumb indentation, various configurations and various configurations of thumb indentations can be used and the particular configuration is not critical. The particular configuration shown is used for aesthetic reasons. The housing includes at least one contact area for aligning the housing with a portion of a patient's body. This at least one contact area is preferably two spaced apart contact areas positioned on a portion of the housing that extends from a user's hand when properly held in the user's hand for range of motion testing. The contact areas may include a nonslip surface. Within the housing is an inclinometer to measure the angle of the device and produce an angle signal indicative of the measured angle. The range of motion of a body part is determined by measuring the angle of the part at one extreme of movement and measuring the angle of the same part at the other extreme of movement. The difference of the two measurements indicates the range of motion of the body part.

A force applicator coupler removably secures a force applicator to a force transducer which measures the force applied to the transducer by the applicator and produces a force signal indicative of the force applied. The force applicator is positioned against a body part of the patient being tested and force is applied between the patient's body part and the apparatus. Where the force applied is caused by the muscles of the patient, the force applied is a measure of muscle strength. Various force applicators with differing surface configurations may be selectively used for different parts of the body.

Interface circuitry converts the angle signals and the force signals into usable output signals indicative of range of motion or muscle strength. Such usable signals can generate a display of a measurement of range of motion or muscle strength such as on an LCD display included as part of the apparatus and/or may provide signals to a computer for use in a computer program which displays and/or prints out measurements, stores and compares measurements and/or provides reports of measurements and differences in measurements over time, graphs such comparisons of measurements, etc.

The apparatus may be connected by a cable to a computer during taking of measurements, or may transmit measurements during taking of measurements by wireless transmission such as by RF transmission, infrared light transmission, or any other suitable wireless transmission.

THE DRAWINGS

In the accompanying drawings, which show the best mode currently contemplated for carrying out the invention.

DETAILED DESCRIPTION OF THE ILLUSTRATED EMBODIMENTS

Figure 1:
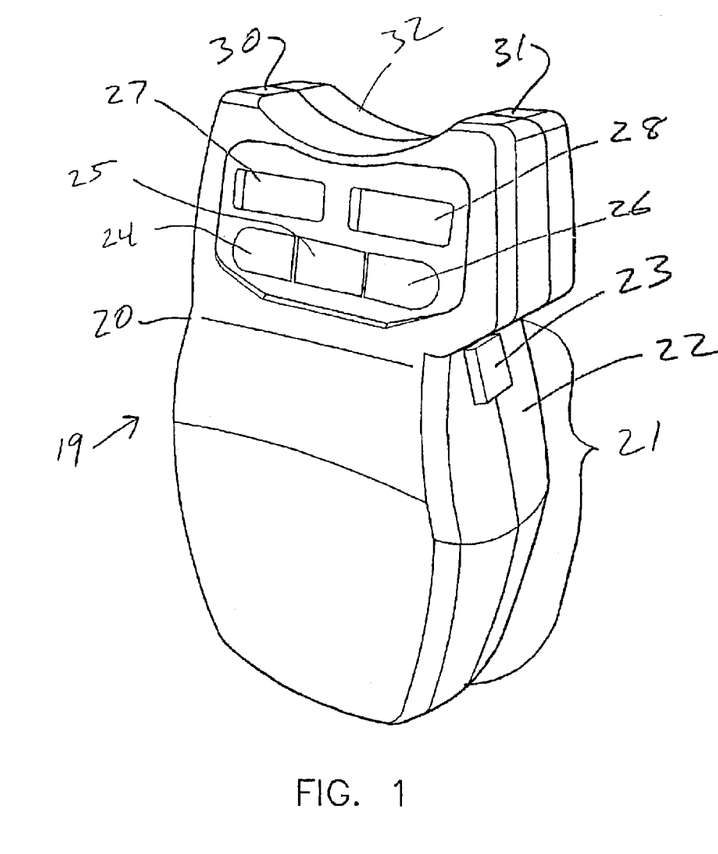
FIG. 1 is a front right side perspective view of an apparatus of the invention.

The invention is a handheld apparatus for selectively measuring range of motion or muscle force of a human patient. In the illustrated embodiment, the apparatus, generally indicated as 19, includes a housing 20 with lower portion 21 sized and configured to be held in the hand of a user. An indentation 22 is provided to comfortably receive the thumb of a user when the apparatus is properly held in the user's hand for range of motion testing with a push button switch 23 which can easily be operated by a user's thumb. When held for muscle strength testing, the index finger rather than the thumb is received in indentation 22. Membrane switches 24, 25, and 26 are accessible to and operable by a user and displays 27 and 28, such as LCD displays (liquid crystal displays), are visible to a user.

While various arrangements of switches may be used, switch 24 may be a reset switch, switch 25, a switch to set the apparatus to muscle strength testing mode, and, once in muscle strength testing mode, can be used to switch back and forth between two detection thresholds, and switch 26 to set the apparatus to angle measurement mode. The displays will display appropriate measurements for the operating mode of the apparatus selected. Switch 23 is used to indicate when an angle measurement is to be accepted for determining range of motion.

For measuring range of motion, the apparatus has a contact area which can be placed against a body part of a patient and which will align the apparatus with the body part. The contact area should be such that it can be aligned against the body part in a repeatable manner so that accurate and repeatable placement against the body part is possible to provide accurate and repeatable range of motion measurements. In the illustrated embodiment, areas 30 and 31 provide contact areas which are placed against the body part to be measured. Areas 30 and 31 are positioned on a portion of the housing that extends from the user's hand when the apparatus is held in the user's hand and are spaced apart by indentation 32 so that the areas 30 and 31 can bridge any irregularities in the body part between the areas 30 and 31 and give two contact points to provide solid contact with the body part. In this way, the device does not rock on the body part which would provide an inaccurate measurement. Areas 30 and 31 can be formed with nonslip surfaces.

In use for measuring range of motion, the patient is positioned with the body part to be measured at one extreme of movement. The areas 30 and 31 are placed against the body part or a part connected to the body part, such as the head when range of motion of the neck is measured, and button 23 is depressed to initiate the measurement. The angle of the apparatus is noted and the body part is moved to the other extreme of movement. The apparatus is similarly positioned against the body part and button 23 is depressed to note the new angle of the apparatus. The difference between the two noted angles is calculated to provide an indication of the angular movement of the body part. This provides a measurement of the range of angular motion through which the body part can move.

Figure 6:
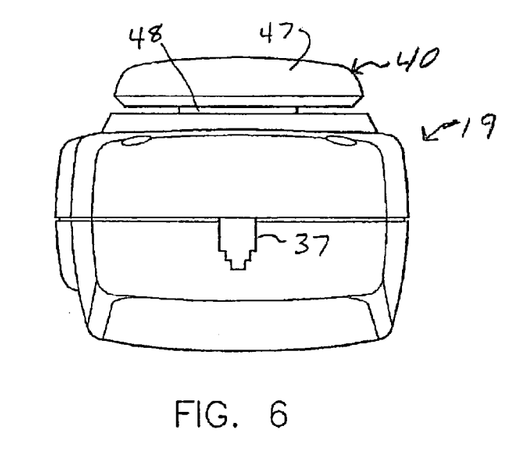
FIG. 6, a bottom plan view of the apparatus of FIGS. 3 and 4.
Figure 7:
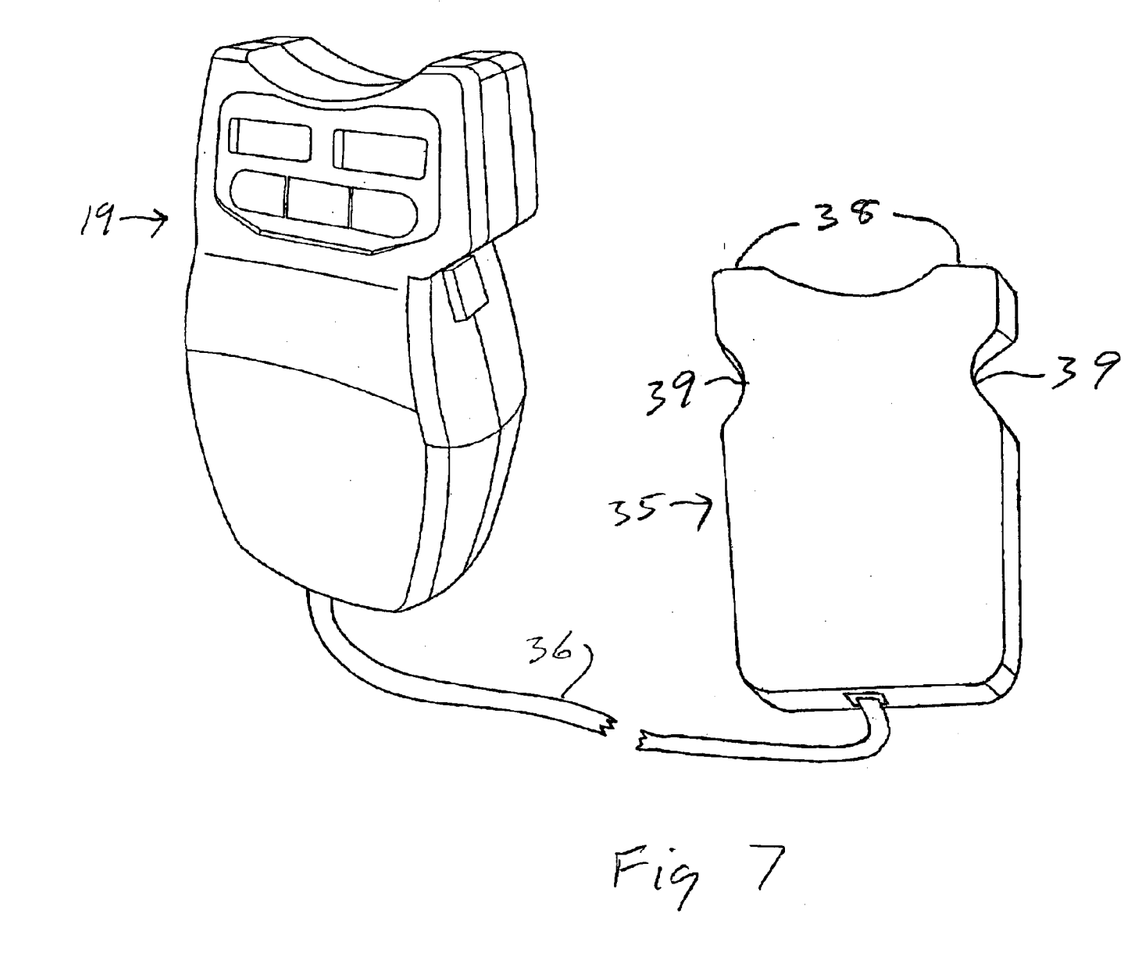
FIG. 7, a perspective view of the apparatus of FIG. 1 with a slave apparatus connected thereto.

In measuring the range of motion of some body parts, movement of an additional body part affects the measurement obtained. For example, if the range of motion of the elbow is being measured, it is important that the arm does not move at the shoulder. This usually is not a problem. However, a slave range of motion apparatus or unit 35, FIG. 7, can be connected by cable 36 to and used with apparatus 19 shown, which is used as the master apparatus or unit, and the angle measured at each extreme of movement will be the difference between the measured angles of the master and slave units. With proper placement of the slave unit, the master slave arrangement will compensate for movement of other body parts. For example, with the movement of the elbow, if movement of the arm from the shoulder occurs and the slave unit is against the arm between the elbow and the shoulder, movement of the arm from the shoulder is automatically compensated for to give a measurement of movement of only the elbow. A modular telephone connector 37, FIG. 6, may be used to removably connect cable 36 and slave unit 35 to master unit 19. Slave unit 35 also includes two contact areas 38 for positioning against the patients body part to be measured, and indentations 39 for holding and manipulating the slave unit.

Figure 2:
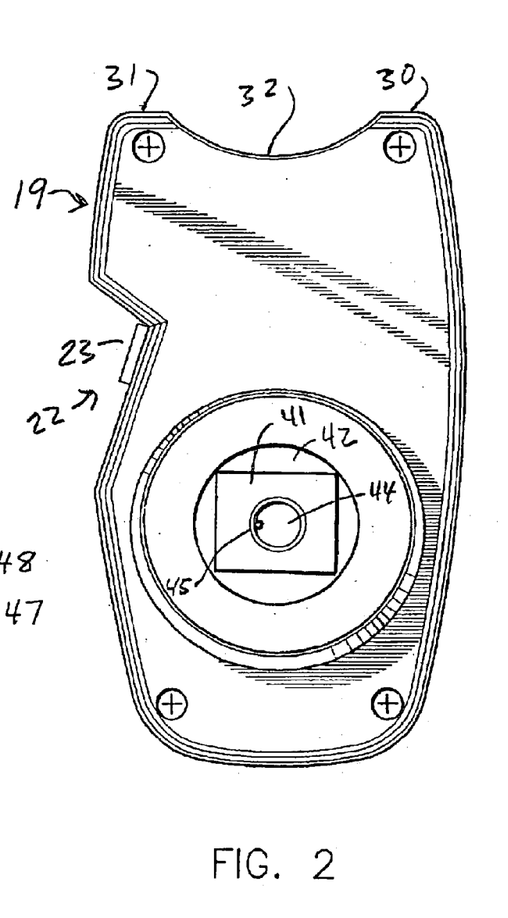
FIG. 2, a rear elevation of the apparatus of FIG. 1 without a force applicator attached.
Figure 3:
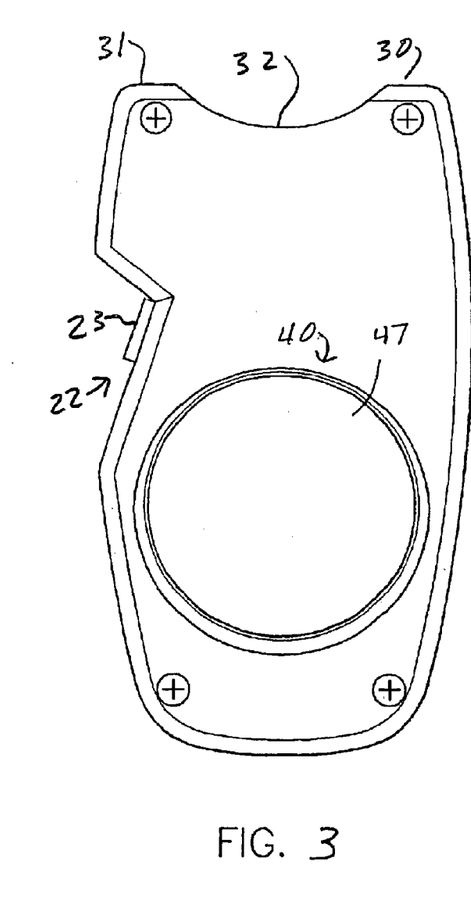
FIG. 3, a rear elevation similar to that of FIG. 3, showing a force applicator attached to the apparatus and extending from the rear thereof.
Figure 4:
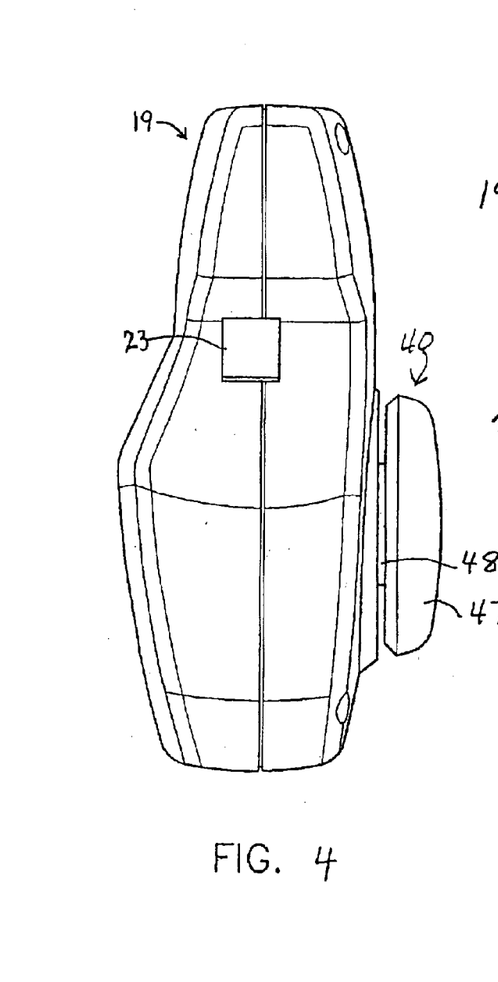
FIG. 4, a right side elevation of the device of FIG. 1 with the force applicator of FIG. 3 attached.
Figure 5:
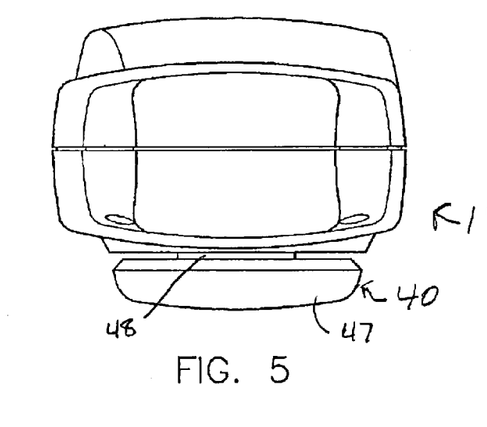
FIG. 5, a top plan view of the apparatus of FIGS. 3 and 4.

For use in measuring muscle strength, a force applicator 40, FIGS. 3–6 and 8, is secured to a force transducer 41, FIG. 2, located in the housing and accessible from the rear of the housing through opening 42. While the force applicator could be permanently secured to the apparatus, it is preferred that the force applicator be removably secured to the force transducer so it can be changed as desired for an applicator which best fits the particular body part being tested. Thus, force applicator 40 includes a mounting shaft 43, FIG. 8, which fits into applicator receiving hole 44, FIG. 2. A spring loaded piston 45 is mounted in transducer 41 with an end extending into receiving hole 44. The end of applicator mounting shaft 43 is chamfered as at 46 so it engages and pushes spring loaded piston 45 away from hole 44 as mounting shaft 43 is pushed into hole 44. Piston 45 bears against shaft 43 to hold it in hole 44 by friction until force applicator 40 is pulled from hole 44. If desired, an annular groove can be provided around shaft 43 to receive the end of piston 45 for a more secure mounting of force applicator 40 in transducer 41.

Figures 8, 9:
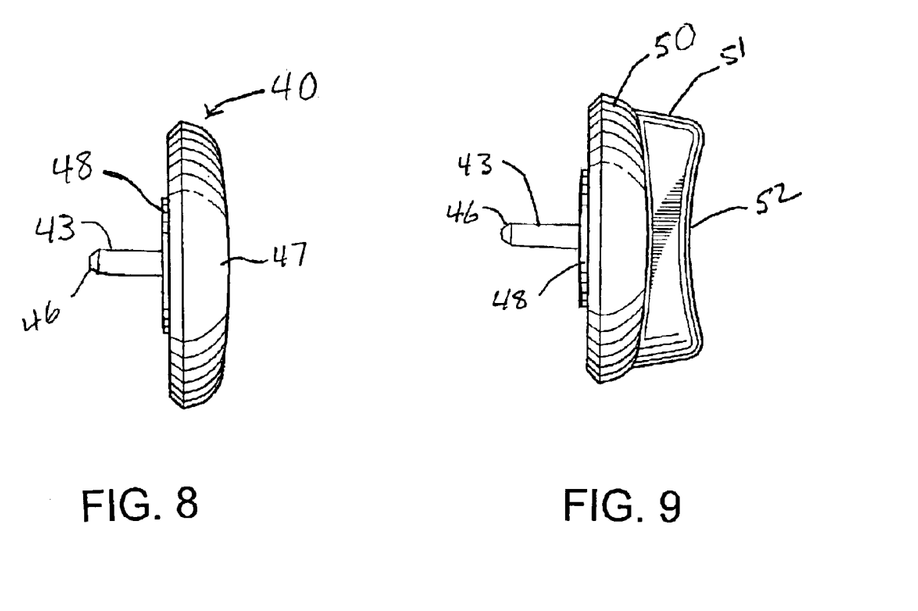
FIG. 8, a side elevation of the force applicator of FIGS. 3–6.
FIG. 9, a side elevation of another embodiment of force applicator.
Figure 10:
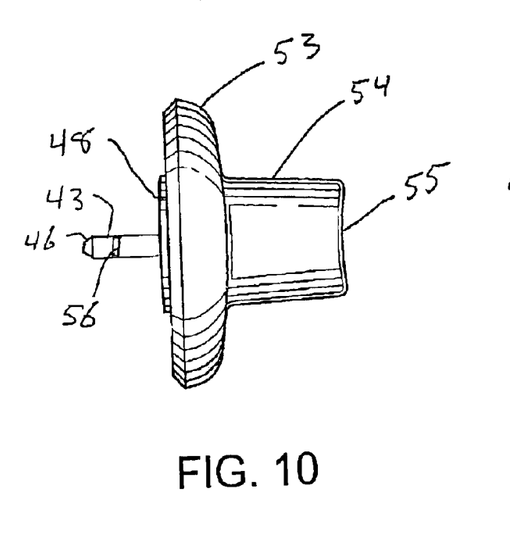
FIG. 10, a side elevation of another embodiment of force applicator.

Force applicator 40 also includes an applicator pad 47 which actually contacts the body part to be tested and a disc 48 extending from mounting shaft 43 adjacent pad 47. Disc 48 contacts transducer 41 and spaces pad 47 from apparatus housing 20 so that it does not contact housing 20 and interfere with the force measurements. FIGS. 9 and 10 show two variations of force applicators that may be used for muscle strength testing. Each is similar to applicator 40 except for the shape of the pad which is differently configured to fit different parts of the body. Pad 50 of the applicator of FIG. 9 has an extension 51 extending across pad 50 with an inwardly curved surface 52. Pad 53 of the applicator of FIG. 10 has a narrower extension 54 extend across an intermediate portion of pad 53 with an inwardly curved surface 55. A user selects the force applicator which best fits the body part to be tested. FIG. 10 also shows a groove 56 in receiving shaft 43 for engagement by piston 45.

Figure 11:
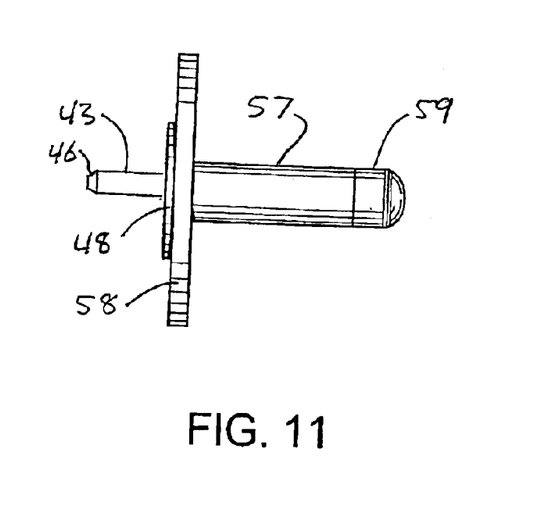
FIG. 11, a side elevation of still another embodiment of force applicator.

FIG. 11 shows a fourth applicator which may be used for tender point evaluation for testing for fibromyalgia. The applicator of FIG. 11 is similar to those of FIGS. 8–10, but includes a further shaft 57 extending outwardly from disc 58 adjacent disc 48 with a small pad 59 on its end. This pad 59 has relatively small surface area. Disc 58 is not necessary, but is convenient because it is actually present in the applicators of FIGS. 8–10, but is not visible because it is covered by the respective pads 47, 50, and 53. In use, a user places pad 59 against selected locations on a patient's body and applies force to the apparatus which applies the force to the body location through pad 59. Force is applied until either a desired force is applied without pain to the patient or until pain is felt by the patient and a reading of the force applied to create pain is recorded.

Figure 12:
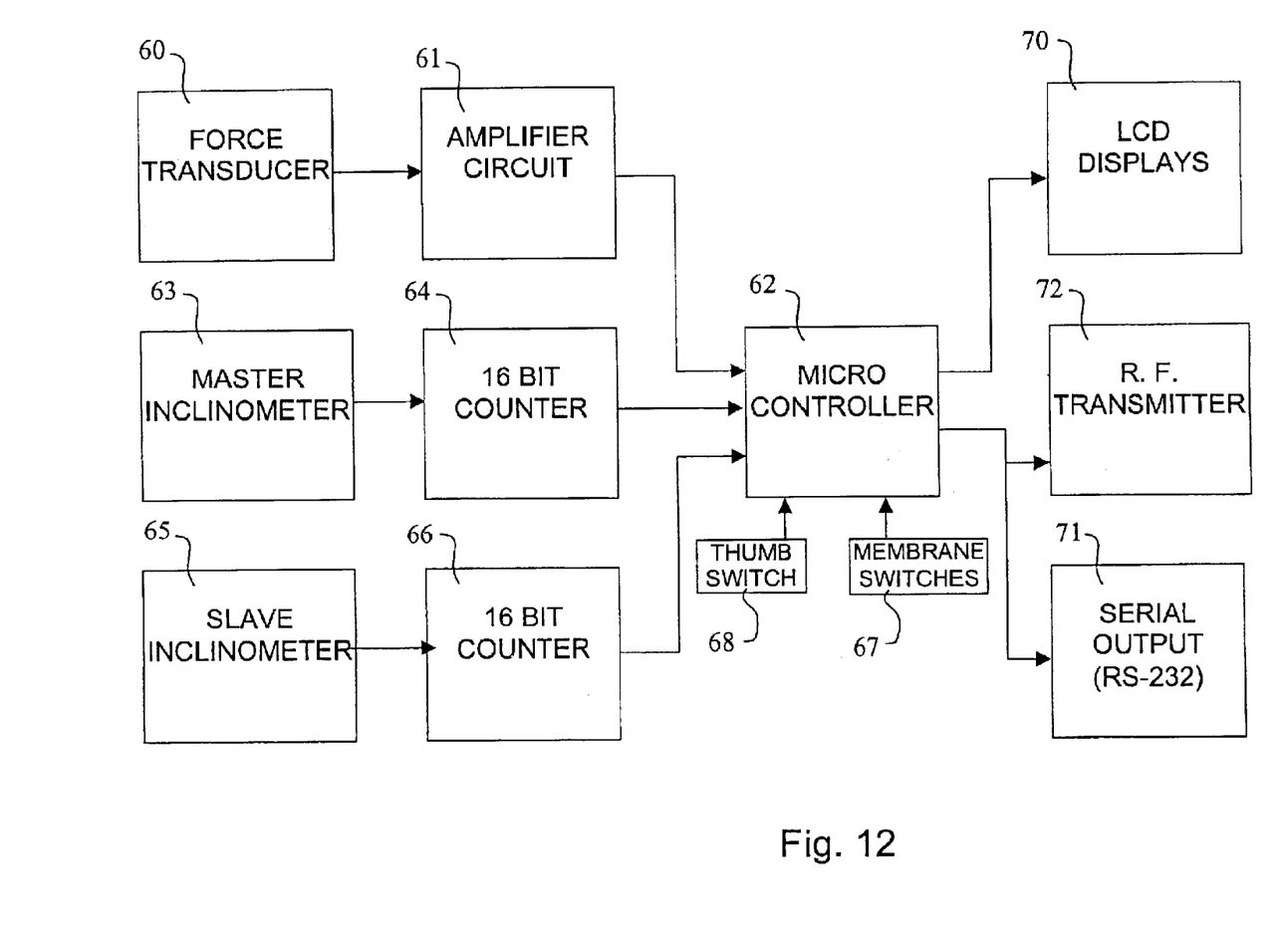
FIG. 12, a block diagram of circuitry of the invention.

FIG. 12 shows a basic block diagram of an apparatus of the invention. A selected force applicator as shown in FIGS. 8–11 is coupled through a force applicator coupling to a force transducer 60. For force transducer 41 previously illustrated and described, the applicator coupling comprises receiving hole 44. The force transducer 60 produces a force signal indicative of the force applied to the force transducer. The force signal is amplified by amplifier 61 and the amplified force signal is fed to a microprocessor 62. A inclinometer 63, such as a U.S. Digital Model T2-3600 inclinometer, is positioned in the apparatus to provide an angle signal indicative of the angle of the apparatus. The angle signal as produced by the indicated inclinometer is a series of pulses that indicate angular movement. The angle signal is connected to a sixteen bit counter 64 which counts the pulses from the inclinometer. The count output is an indication of the angular movement of the apparatus from an arbitrary start position and is connected to the microprocessor 62. An optional slave inclinometer 65 is connected to sixteen bit counter 66 which is also connected to microprocessor 62. Membrane switches 24, 25, and 26 of FIG. 1 are indicated as a group as inputs 67 to microprocessor 62, and thumb switch 23, FIG. 1, is indicated as input 68 to microprocessor 62.

Microprocessor 62 provides output signals to displays 27 and 28, FIG. 1, indicated as displays 70, and can provide computer compatible output signals directly to a computer through a wire connected to a serial output port 71, or to a wireless transmitter such as an RF transmitter 72.

Microprocessor 62 is programmed to control operation of the apparatus in response to input through the membrane switches 67 and the thumb switch 68. Although a master on-off switch could be provided, in the illustrated apparatus, the microprocessor is programmed so if no inputs are received by the microprocessor for a predetermined time period, such as three minutes, the microprocessor puts the circuitry into sleep mode by turning everything off. This conserves power. Then, upon receiving an input from the reset switch 24, the circuit is again activated. When the apparatus is in the force measurement mode, a force is sensed by the force transducer and is sent to the microprocessor. The microprocessor is programmed so that if the apparatus is in the range of motion mode, operation of the force measurement switch 25 puts the circuitry into force measurement mode. When in force measurement mode, further operation of the force measurement switch 25 changes back and forth between two threshold values.

Operation is controlled so that when force is applied through the force applicator to the force transducer 60, the microprocessor generates display signals to indicate on the display the force measured. After the measured force exceeds the set threshold, the force signals are displayed on the display substantially as measured until the measured force drops below the set threshold. At that time, the microprocessor assumes that the force measurement has been taken and displays the maximum force measured during the time the measurements were above the threshold. When force measurements again exceed the set threshold, the cycle starts over and measurements are displayed until the measured force drops below the threshold and again the maximum force measured during that period is displayed.

When the inclinometer or range of motion switch 26 is activated, the circuitry switches to range of motion mode. In such mode, the microprocessor 62 reads the sixteen bit counter 64 and, if the slave unit is connected, also reads counter 66. It causes display of angle measurements on displays 27 and 28. When thumb switch 23 is actuated, meaning that a range of motion measurement should be started, the microprocessor notes the angle value and continues to measure angles. When switch 23 is again actuated, meaning that the range of motion measurement should be completed, the second measured angle value is noted and the microprocessor calculates and displays the difference between the two noted angles measured which indicates the angular range of motion. Also upon actuation of switch 23, the microprocessor, if the apparatus is connected to transmit signals to a computer, indicates actuation of switch 23, such as by a change of a bit in the signals sent to the computer, to indicate actuation of the switch to the computer. This allows the computer to make its own calculation of range of motion. Pressing the reset switch will reset the microprocessor and zero the displays.

Figure 13:
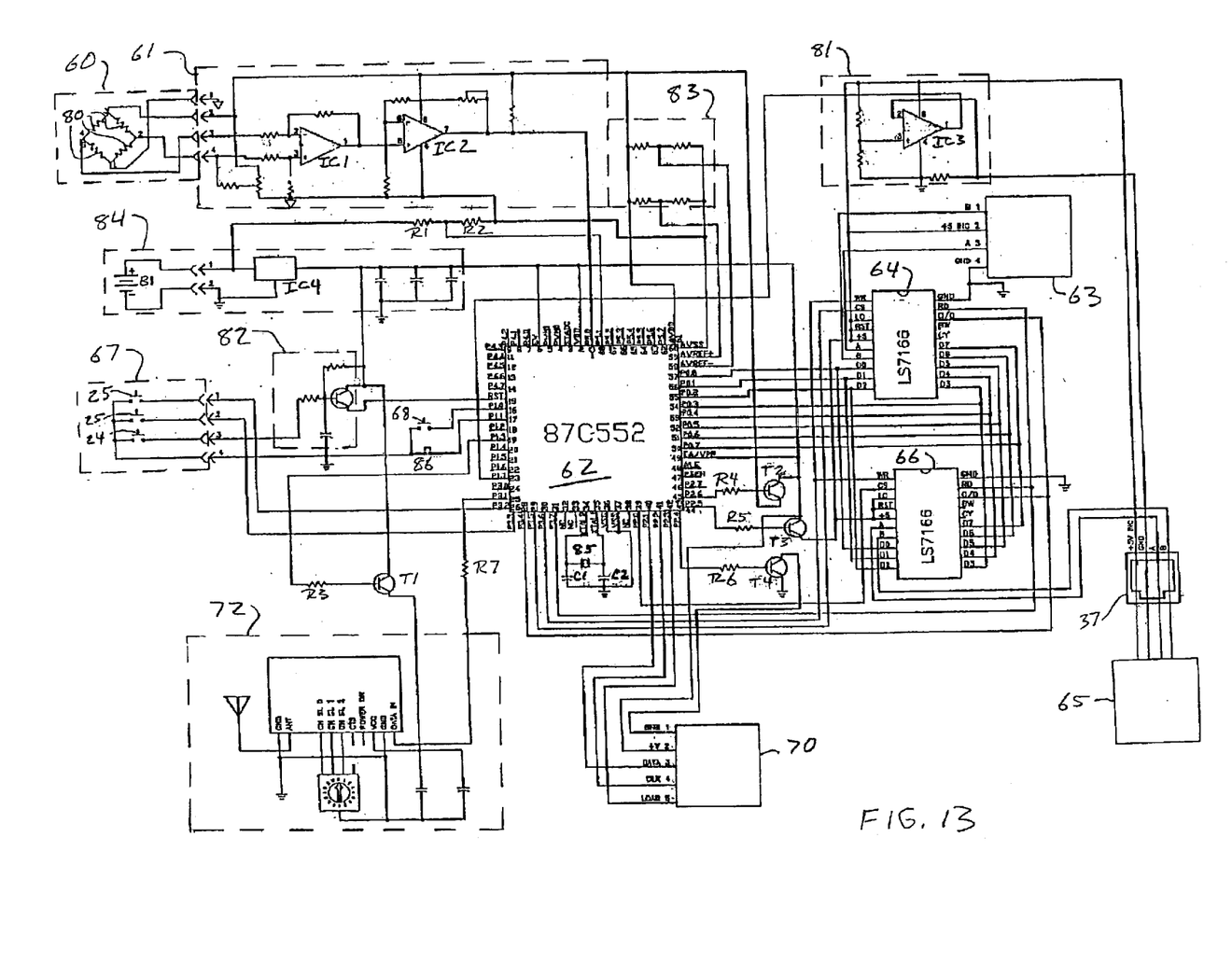
FIG. 13, a circuit diagram of circuitry of the invention including an RF transmitter for communication with a computer and a connection for a slave inclinometer.

FIG. 13 shows circuitry for the blocks in FIG. 12 using the RF transmitter for communication with a computer, as well as some additional circuitry. The force transducer 60 is a bridge circuit of strain gauges 80. This is connected to amplifier 61 which is a standard two stage amplifier including operational amplifiers IC1 and IC2. The resistors set the gain for the amplifiers. The output of IC1 is connected to microprocessor 62. Master inclinometer 63 is connected to sixteen bit counter 64 which is connected to microprocessor 62. Slave inclinometer 65, if provision is made for such slave unit, is connected, when desired, through modular connector 37 to sixteen bit counter 66. Counter 66 is connected to microprocessor 62. Circuit block 81 which includes operational amplifies IC3 connected as a current sensor detects and signals microprocessor 62 when slave inclinometer 65 is plugged into the apparatus. Circuitry 82 operates when reset switch 24 is actuated to reset the circuitry. The voltage dividers in circuitry 83 provide positive and negative reference voltages for use in converting the analog muscle strength signals to digital signals. Circuitry 84 is the power supply circuitry with battery B1 and voltage regulator IC4. The capacitors filter the power from the regulator. Resistors R1 and R2 form a voltage divider to produce a reference voltage for converting the analog voltage value of the battery to a digital signal. Resistor R3 and Transistor T1 operate to turn on the RF transmitter circuitry 72 when needed. Resistor R4 and Transistor T2 turn on the amplifier circuitry 61, resistor R5 and transistor T3 turn on the inclinometers 63 and 65 and counters 64 and 66, and resistor R6 and transistor T4 turn on the display. Resister R7 is a current limiting resister in the data line from the microprocessor to the RF transmitter. Crystal 85 with capacitors C1 and C2 set the clock rate for the microprocessor 62. Reference number 86 represents a jumper that can be placed in the circuitry when desired to read out the force measured by force transducer 60 in units of Newtons rather than in pounds.

Figure 14:
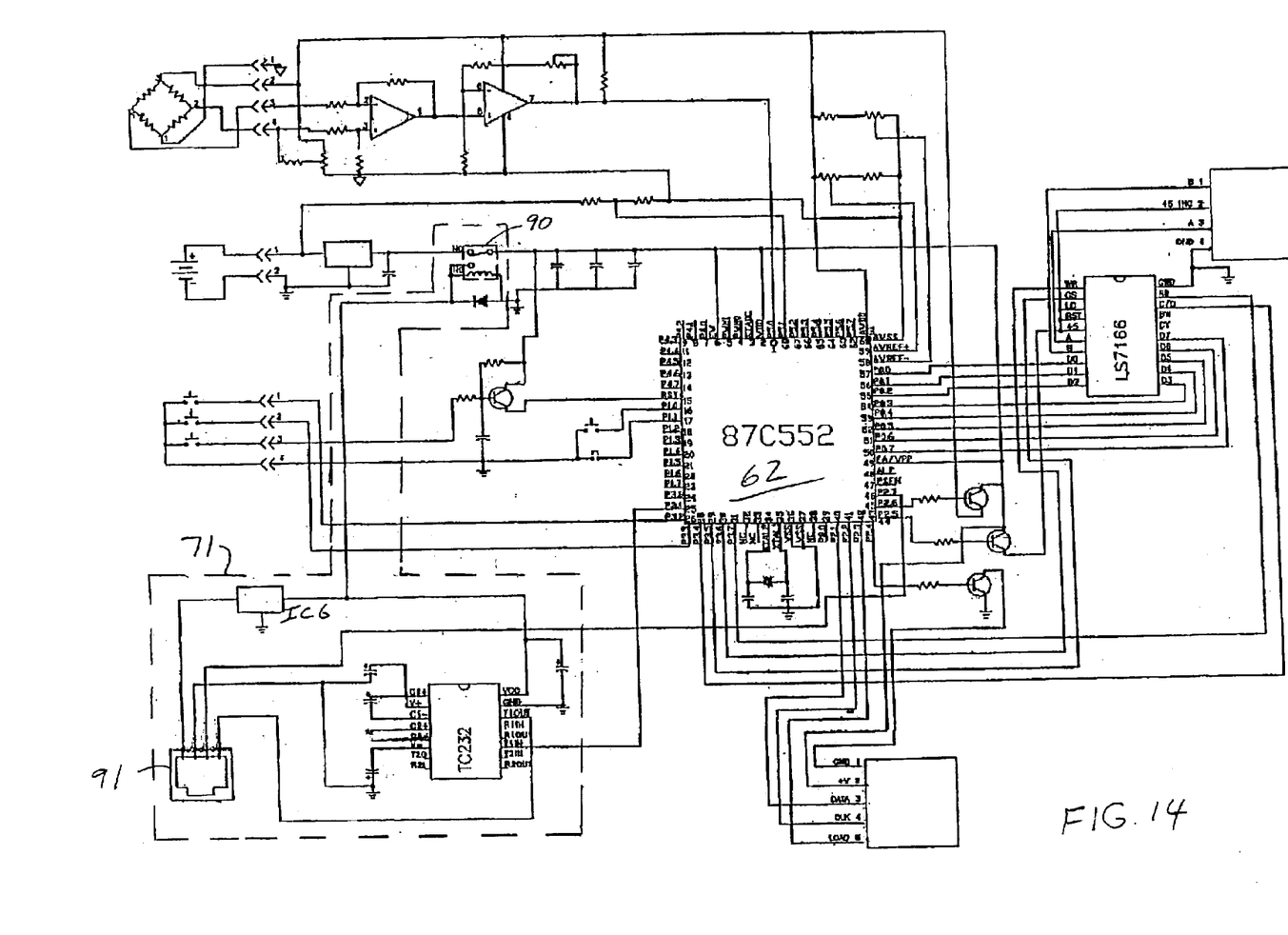
FIG. 14, a circuit diagram similar to that of FIG. 13, but showing a different circuit for communication with a computer and only one inclinometer.

FIG. 14 shows circuitry the same as that of FIG. 13, except that a serial data output to a cable plug rather than the RF transmitter is shown for communication with a computer, and no provision is shown for connection of a slave inclinometer. The circuitry of block 71 includes a relay 90 which operates when a cable is connected to modular connector 91 to supply power through a voltage regulator IC6 to the plug as well as to IC7 which is connected to the data line from the microprocessor to condition the data for transmission the computer. It is currently preferred to provide an apparatus with either a cable connection to a computer and no provision for a slave unit or an apparatus with the slave unit and a wireless communication with a computer. This provides a choice of option and price. However, an apparatus including provision for the slave unit and both computer communication options can be offered. The apparatus can be used with computer software currently available from Hoggan Health Industries in Draper, Utah, or with software available from Myo-Logic Diagnostics, Inc. The apparatus can also be used as a stand alone unit where the measurements are recorded by hand from the apparatus displays.

Whereas the invention is here illustrated and described with reference to embodiments thereof presently contemplated as the best mode of carrying out the invention in actual practice, it is to be understood that various changes may be made in adapting the invention to different embodiments without departing from the broader inventive concepts disclosed herein and comprehended by the claims that follow.

We claim:

1. Apparatus for selectively testing muscle strength and range of motion of body parts of a patient, comprising:
    a housing having at least one contact area for aligning the housing with a portion of a patient's body;
    an inclinometer to measure the angle of the apparatus and produce an angle signal indicative of the measured angle;
    a force transducer;
    a force applicator coupler to secure a force applicator to the force transducer whereby the force transducer will measure the force applied to the transducer by the applicator and produce a force signal indicative of the force applied to the transducer;
    interface circuitry for converting the angle signals and the force signals to usable output signals.

2. Apparatus for selectively testing muscle strength and range of motion of body parts of a patient according to claim 1, additionally including a display, and wherein the usable output signals operate the display to indicate the selected measured muscle strength or measured range of motion.

3. Apparatus for selectively testing muscle strength and range of motion of body parts of a patient according to claim 2, wherein the display is an LCD display.

4. Apparatus for selectively testing muscle strength and range of motion of body parts of a patient according to claim 2, wherein the usable output signals include signals compatible with selected computer programs for processing such signals.

5. Apparatus for selectively testing muscle strength and range of motion of body parts of a patient according to claim 4, additionally including a plug for receiving a cable connected to a computer.

6. Apparatus for selectively testing muscle strength and range of motion of body parts of a patient according to claim 4, additionally including a memory to store the usable output signals for later transmittal to a computer.

7. Apparatus for selectively testing muscle strength and range of motion of body parts of a patient according to claim 4, additionally including a wireless transmitter for transmitting the usable signals.

8. Apparatus for selectively testing muscle strength and range of motion of body parts of a patient according to claim 7, wherein the transmitter is an RF transmitter.

9. Apparatus for selectively testing muscle strength and range of motion of body parts of a patient according to claim 7, wherein the transmitter is an infrared light transmitter.

10. Apparatus for selectively testing muscle strength and range of motion of body parts of a patient according to claim 1, wherein the usable output signals include signals compatible with selected computer programs for processing such signals.

11. Apparatus for selectively testing muscle strength and range of motion of body parts of a patient according to claim 10, additionally including a plug for receiving a cable connected to a computer.

12. Apparatus for selectively testing muscle strength and range of motion of body parts of a patient according to claim 10, additionally including a memory to store the usable output signals for later transmittal to a computer.

13. Apparatus for selectively testing muscle strength and range of motion of body parts of a patient according to claim 10, additionally including a wireless transmitter for transmitting the usable signals.

14. Apparatus for selectively testing muscle strength and range of motion of body parts of a patient according to claim 13, wherein the transmitter is an RF transmitter.

15. Apparatus for selectively testing muscle strength and range of motion of body parts of a patient according to claim 13, wherein the transmitter is an infrared light transmitter.

16. Apparatus for selectively testing muscle strength and range of motion of body parts of a patient according to claim 1, wherein the at least one contact area is two spaced apart contact areas.

17. Apparatus for selectively testing muscle strength and range of motion of body parts of a patient according to claim 16, additionally including a nonslip surface on the contact areas.

18. Apparatus for selectively testing muscle strength and range of motion of body parts of a patient according to claim 1, wherein the housing is configured to fit into and be held by a user's hand, wherein a thumb operated switch determines when a measurement is to be made, wherein the housing has an indentation aligned with a user's thumb when the housing is properly held by a user, and the thumb operated switch is located in the indentation to be easily operated by a user's thumb.

19. Apparatus for selectively testing muscle strength and range of motion of body parts of a patient according to claim 18, wherein the at least one contact area is positioned on a portion of the apparatus that extends from a user's hand when the apparatus is properly held by a user.

20. Apparatus for selectively testing muscle strength and range of motion of body parts of a patient according to claim 19, wherein the at least one contact area is two spaced apart contact areas.

* * * * *